United States Patent [19]

Tellier et al.

[11] Patent Number: 4,460,692
[45] Date of Patent: Jul. 17, 1984

[54] MICROEMULSION OF NUTRIENT SUBSTANCES

[75] Inventors: Jacques Tellier, Lons; Andreé Sirvins, Pau; Jean-Claude Gautier; Bernard Tramier, both of Billére, France

[73] Assignee: Societe Nationale Elf Aquitaine (Production), France

[21] Appl. No.: 471,768

[22] Filed: Mar. 3, 1983

Related U.S. Application Data

[62] Division of Ser. No. 302,961, Sep. 17, 1981, Pat. No. 4,401,762.

[30] Foreign Application Priority Data

Sep. 19, 1980 [FR] France ................................. 80 20178
Sep. 1, 1981 [FR] France ................................. 81 16626

[51] Int. Cl.³ ............................................. C12N 1/00
[52] U.S. Cl. ................................... 435/243; 435/253; 435/254; 252/8.55 D
[58] Field of Search ............... 435/281, 243, 253, 254; 252/309, 8.55 D

[56] References Cited

U.S. PATENT DOCUMENTS

| | | | |
|---|---|---|---|
| 3,268,413 | 8/1966 | Laine et al. | 435/281 |
| 3,536,136 | 10/1970 | Jones | 252/8.55 D |
| 3,728,279 | 4/1973 | Salomone | 435/281 X |
| 3,964,548 | 6/1976 | Schroeder et al. | 252/8.55 D |
| 3,981,361 | 9/1976 | Healy | 252/8.55 D |
| 4,125,156 | 11/1978 | Glinsmann | 252/8.55 D |
| 4,146,499 | 3/1979 | Rosano | 252/8.55 D |

Primary Examiner—Robert A. Yoncoskie
Attorney, Agent, or Firm—Ostrolenk, Faber, Gerb & Soffen

[57] ABSTRACT

There is disclosed a nutrient composition to be added to a hydrophobic medium for culturing microorganisms comprising a micro-emulsion of an aqueous solution of nutrient material in a liquid immiscible with water. As the source of nitrogen, compounds soluble in water are used, such as urea or ammonium nitrate, sulphate or phosphate, and, as the source of phosphorus, compounds soluble in water are used. The medium should also contain a directly-assimilable source of carbon. Application of this composition for culturing of microorganisms allows operations to be carried out which comprise the degrading of hydrocarbons covering an area of water or ground; an application of particular interest for operations is for combatting oil pollution of the sea by biological degradation.

20 Claims, No Drawings

MICROEMULSION OF NUTRIENT SUBSTANCES

This is a division of application Ser. No. 302,961 filed Sept. 17, 1981 now U.S. Pat. No. 4,401,762.

The present invention relates to a novel type of microemulsion, namely the thermodynamically-stable microemulsion of an aqueous solution of nutrient materials, the external phase of which is constituted by a hydrophobic medium. It comprises a process of production of such a microemulsion and applications of it in areas of utilization of microorganisms, particularly in the culture of microorganisms in a hydrophobic medium.

Industrial operations making use of cultures of various microorganisms, particularly bacteria and fungi, are of particular interest at the present time. Numerous food industries, manufactures of medicaments, purifications etc. are based upon such operations. Most frequently, the operation comprises two stages: Firstly, culture of the microorganism concerned takes place in an appropriate nutrient medium to achieve growth of a sufficiently numerous population; in the second stage, this population is placed in contact with materials which it is desired to subject to the action of the microorganisms. Operations in vessels do not involve special difficulties from the standpoint of, preliminary culture, that is, multiplication, being effected—depending upon the case—in a separate enclosure or in the same vessel where the second operative phase takes place. In contrast, when the operations are carried out in nature, on large areas of ground or water, as is the case for example in the elimination of hydrocarbon slicks by microbiological degradation at sea, on beaches, in flowing water or on lakes, the preliminary multiplication of the microorganisms used presents difficulties. In practice, it is necessary to provide the culture with nutrient materials, that is sources of C, N and P, as well as trace elements, to ensure growth of the organisms in question. When the standard sources, such as hydrides of carbon, nitrates or ammonical salts and phosphates are soluble in water, they cannot remain in the extended superficial layer to be treated, where a strong growth of the microorganisms used should occur. These substances diffuse into the water or the adjacent ground and are thus under-used by the culture.

To remedy this, various methods have been employed up to the present. One of them consists in enrobing in paraffin granules of the nitrogenous compound and solid phosphates in order to make them available to the microorganisms in this form, as indicated in U.S. Patent Specification No. 1,959,127. In a variant, according to the U.S. Patent Specification No. 3,883,397, the lipophilic enrobing compound is a fatty acid salt in place of paraffin. However, these methods do not allow the microorganisms to have the desired nutrient rapidly available. The fatty enrobing material is difficult to penetrate, that is, to degrade, in the absence of external nitrogen and phosphorus. Also, the action of bacteria or fungi itself is slow and requires weeks or months. Another proposed solution consists in utilizing, as the sources of N and P, compounds insoluble in water but soluble in hydrocarbons, particularly phospho-amino-lipids, as described in French Published Specification No. 2,172,796. However, nitrogenous compounds soluble in oil generally have a very low nitrogen content and, under these circumstances, the biological degradation of petroleum hydrocarbons in the sea requires two to three months. In French Published Specification No. 2,230,401, the use has also been indicated of amides, organic ammonium salts and phospho-amino-lipids in solution in a petroleum solvent, the solution being emulsified in water. The emulsion obtained is atomized over a hydrocarbon oil slick floating on the water for biodegradation of the slick. This method requires large proportions of the aqueous emulsion and the result is only obtained after several weeks.

The present invention provides a novel solution to the supply of nutrient substances, soluble in water, to a hydrophobic organic layer. Whether this layer—which can be a hydrocarbon—floats on water or is disposed on the ground or on a support comprising a constructional material, the nutrient substances provided according to the invention remain principally in the hydrophobic layer and permit rapid multiplication of the microorganisms if sources of them are present.

The novel process according to the invention consists in making a microemulsion of the water-in-oil type, the internal phase of which is an aqueous solution of nutrient materials and the external phase of which is a liquid immiscible with water, and adding this microemulsion to the hydrophobic layer which is to be degraded. The microemulsion can contain sources of the appropriate microorganisms, if the medium to be treated contains none or does not contain sufficient amounts.

It will be understood, as is known in the art, that the microemulsion contains at least one surface-active agent and an auxiliary agent, which have served in its preparation.

Thus, contrary to the prior technique, the nutrient substances are neither utilized in the solid state nor in solution in a solvent immiscible with water nor in an aqueous macroemulsion, but in the form of a microemulsified aqueous solution in a liquid miscible with the hydrophobic layer to be biodegraded, that is, in the form of microdispersed so-called inverse droplets, the diameter of which ranges from 80 to 600 Ångstroms and in particular from 100 to 200 Ångstroms. This unexpected form leads to the remarkable result that the biodegradation can be realized in several days, in place of the weeks or months required by known processes.

As regards the source of nitrogen, in the microemulsions according to the invention, various compounds soluble in water and assimilable by the microorganisms can be employed. These are, for example, ammonium nitrate, sulphate and/or phosphae, urea, proteins, peptones, etc. As urea is the source richest in nitrogen and is very soluble in water, it is particularly appropriate because it allows highly concentrated aqueous solutions to be produced. For example, solutions of urea containing 10% to 60% by weight can be employed, that is, 11 to 150 parts of urea per 100 parts of water.

Phosphorus can also be provided in the solution in one of the customary forms, namely alkali metal or ammonium phosphates or phosphites. According to a particular embodiment of the invention, phosphorus is provided in the form of a surfactant compound, such as a higher alkyl phosphate or a lecithin, for example. The source of phosphorus and the surface-active agent of the microemulsion are thus in the same molecule.

In various industrial operations comprising the culture of microorganisms, it is necessary for the pH of the medium to be adjusted to the value most favourable to bacterial growth. In general, this pH should be in the vicinity of neutrality and it is possible to add either phosphoric acid as a source of phosphorus, if the medium has to be acidified, or ammonia as a source of nitrogen, if the medium has to be neutralized by a base.

In the case of bacterial degradation of hydrocarbons by the microorganisms cited below, the need for phosphorus is much less than for nitrogen; expressed in weight, the P/N ratio can range from 0.02 to 0.2 and preferably from 0.05 to 0.15. From the standpoint of growth, the most favourable P/N ratios are those as near as possible to 0.05.

When the liquid immiscible with water and preferably lipomiscible, forming the external phase of the microemulsion, or the hydrophobic layer to be degraded is utilizable by the microorganisms as the source of carbon, it is no longer necessary to add other assimilable carbon compounds to the microemulsion. However, if the external phase and the layer to be degraded are attacked with difficulty by the microorganisms, at least at the beginning, it is useful to include in the nutrient solution a readily-utilizable carbon source, for instance soluble hydrides of carbon, thus allowing rapid onset of multiplication of the microorganisms.

As in all cultures, trace elements are necessary, particularly salts of Fe, Mg, K etc and, a very small dose can be added to the nutrient solution, in known manner.

It can be seen that, in order to obtain a microemulsion according to the invention, a surface-active compound capable of producing one is necessary. The choice of a suitable compound, by a person skilled in the art, can be made from various groups of nontoxic surface-active agents for the microorganisms present. For example, fatty alcohol sulphates, sulphosuccinates, oxyethylenic sorbitan esters, oxyethylenic alcohols, acids or oils, esters of saccharose, amino-acids, alpha-amido-amino acids, taurines, sarcosines, polyglycols, higher alkyl phosphates etc. can be used. This list is not limitative and other surfactants can be utilized, in particular those which have dispersant properties vis-a-vis hydrocarbons.

Preferably, the hydrophilic-lipophilic balance of the emulsifying agents employed is from 10 to 17 and most preferably from 11 to 15.

When operations are concerned which are carried out outside, the surfactant itself must be biodegradable, in order to avoid environmental pollution.

As with the surfactants, the choice is equally vast as regards the co-surfactant necessary for the formation of the microemulsion. Such co-agents are well-known in the art and thus they do not need to be listed here. It can merely be noted, in a non-limitative way, that it is possible to use nitrogenous compounds, such as carbamates, amides or amine salts. The viscosity of the microemulsion can be considerably reduced by the addition of an alcohol, particularly $C_6$ to $C_{12}$, an ether or an ester of a polyol, particularly glycol. This considerably facilitates manipulative operations.

When the external phase of the microemulsion must be miscible with the hydrophobic liquid to be biodegraded, it is necessarily chosen according to the nature of this liquid. In the most important practical case, where the latter is constituted by petroleum hydrocarbons, the lipomiscible external phase can be constituted for example by aliphatic, aromatic or naphthenic hydrocarbons or by so-called mineral oils, that is mixtures of such hydrocarbons. This type of external phase is attacked with difficulty by bacteria, when these have not undergone sufficient adaptation. It is thus preferable to utilize vegetable or animal oils, which can serve as the source of carbon because they are utilizable by microorganisms. These oils or preferably their corresponding fatty acids permit rapid development of the microorganisms necessary for the degradation of the hydrophobic layer, particularly crude petroleum.

The weight ratio between the lipomiscible liquid, that is the external phase of the microemulsion, and the aqueous solution to be emulsified should generally be greater than 0.2 This ratio is selected so that the aqueous solution forms the internal phase. The choice of surfactants and co-surfactants is effected according to the nature of the lipomiscible liquid and depending upon the concentration of the salts dissolved in the aqueous phase. The basis for this are the concepts of formulation of microorganisms, known per se.

The process of the invention is applicable to a large number of microorganisms and in particular to those which allow the degradation of hydrocarbons. Thus, the invention can be applied to the utilization of bacteria such as Pseudomonas, Acinetobacter, Flavobacterium, Artrobacter, Corynebacterium etc. The microorganisms can also be fungi.

While the invention is of great interest for various operations of biodegradation effected outdoors, it can also be of use in various manufacturing operations in vessels, whenever a hydrophobic layer of a substance is employed in the process. For example, it applies advantageously in the manufacture of proteins from hydrocarbons by degradation of the latter with the aid of bacteria and/or fungi. In all cases, the remarkable dispersion of aqueous nutrient substances within the hydrophobic phase, obtained through the invention, leads to a very rapid multiplication of the microorganisms. An appreciable gain in time in these operations thus results.

Among applications in the open, water or ground areas, the most important is the degradation of hydrocarbons distributed accidentally. For the reason explained above, that is the fact that the soluble nutrient substances remain in the layer treated instead of being entrained by the water, the invention has a considerable value for combatting marine pollution. However, the same principle applies to operations such as the cleansing from banks, reservoirs, ground areas, containers etc. of hydrocarbon deposits which pollute them. Other applications comprise the distribution of nutrients on agricultural cultures.

Microorganisms are generally present in the medium being treated. However, it is sometimes necessary to effect seeding, when the initial population is judged to be too low or if the medium contains no appropriate bacteria.

In a particular embodiment of the present invention, urea is utilized as the nitrogenous nutrient substance. It has been found that this compound also plays the part of the co-surfactant and it is thus no longer necessary to add another co-surfactant. On the other hand, as phosphorus can advantageously be provided by alkyl esters of phosphoric acid, which provide surfactant properties, the composition of the nutrient solution is simplified by the fact that it is possible to employ urea and the phosphoric ester without any other additive. It is nevertheless recommendable to add liquids permitting reduction of the viscosity of the microemulsion. Various examples of such additives have been cited above. In a particular embodiment of the invention, the butyl ether of ethylene glycol has given excellent results.

The lipomiscible liquid particularly suitable for the external phase of the microemulsion, according to the invention, can be constituted by one or more esters of fatty acids, such as lauric, myristic, palmitic, arachidic, oleic, stearic, caproic and caprylic acids etc. Glycerides of such acids constitute very readily available industrial products, because they are vegetable and animal oils. Thus, oil such as arachidic, whale, rape, linseed, maize, olive, sesame and tall oils etc, can be used. Fatty acids themselves are particularly suitable, if required in appropriate mixtures, in order to remain liquid at ambient temperatures. Thus fatty acids are useful, particularly those containing $C_6$ to $C_{18}$, such as caproic, oenanthylic, caprylic, lauric, palmitic, oleic, lineoleic or stearic for example. To those fatty materials which are not liquids at ordinary temperatures, it is suitable to add hydrocarbons, for example petroleum or gas oil in the proportion of about 5% to 50%. Fatty alcohols, that is from $C_6$ to $C_{24}$, are equally suitable.

In a particular case, where the aqueous solution contains urea and lauryl and/or oleyl phosphates marketed for example by Hoechst under the name "Hostaphat", the preferred nitrogen content of the entire microemulsion is about 4% to 10% by weight or most preferably 5% to 8%. The weight ratio of nitrogen in the lipomiscible liquid is generally from 0.1 to 0.4 and preferably 0.15 to 0.35.

In a general manner, the preferred microemulsions according to the invention comprise by weight 10% to 30% of water, 4% to 10% to assimilable nitrogen in the form of nitrogenous compounds, 5% to 35% of a $C_{10}$ to $C_{18}$ alkyl phosphate or an ethoxylated phenol alkyl phosphate, 0% to 20% of an alkyl ether of an alkylene glycol and 20% to 50% of an aliphatic ester, acid and/or alcohol. The last compounds can comprise liquid hydrocarbons, such as petroleum or its derivatives, for example in the ratio of 5% to 90%.

A variant of the invention comprises an improvement which allows a very rapid action of the microorganisms to be obtained. This renders possible the degradation of hydrocarbons in a very short time, by utilizing for this purpose a very large number of microbes. It has been discovered that, while the best nutrient substance is urea, a part of the microorganisms normally present in seawater and capable of degrading hydrocarbons do not develop and consequently do not participate in the desired degradation. According to the present variant, this fraction of the microorganisms which remain "inactive" can be caused to develop and participate in the degradation of the hydrocarbons, if the nitrogenous nutrient material is accompanied by one or more nitrogenous materials of a chemical composition substantially different from the first. Particularly favourable results are obtained when the first nutrient material is urea and the second is constituted by one or more amino-acids.

It follows that a microemulsion according to the invention intended for the microbiological treatment of a hydrocarbon material preferably contains an aqueous solution of at least two nitrogenous compounds which are substantially different from the chemical standpoint. Thus, for example, if the first nutrient substance is a salt such as ammonium sulphate, phosphate or nitrate, the second is constituted by an amine, an amide, a protein, an amino-acid or another non-ammoniacal compound.

When the nutrient solution comprises urea, the second nitrogenous compound is, for example, ammonium sulphate, phosphate or nitrate or an amino-lipid and particularly an amino-acid. The relative proportions of the two kinds of nitrogenous materials can vary largely, depending upon the nature of the microbial flora of the medium where the process of the invention is applied. Most frequently, the effective proportion of urea, expressed as nitrogen, is from 50% to 99% of the total nitrogen, that is the nitrogen of the amino-acid represents 50% to 1%. In certain aqueous media, about 1% to 10% of nitrogen can be sufficient in this second form, in order to obtain excellent results.

The amino-acids advantageously utilizable according to the present invention can be selected from all those which are found in nature and from synthetic amino-acids. By way of non-limitative examples, use can be made of glycine, alanine, serine, cysteine, valine, glutamine, leucine, lysine, arginine, prolie, tyrosine, aspartic and glutamic acids etc. For reasons of economy, it is useful to utilize the materials obtained from natural products which generally contain a series of several amino-acids. This is the case for example with wines made from sugar beet, extracts obtained by the maceration of various plants, particularly maize cobs, yeast extracts, products of the hydrolysis of proteins, dairy by-products etc.

The invention leads to the unexpected conclusion that, if a nitrogenous nutrient material gives good results alone and if the same applies to another nitrogenous material of a different chemical nature when used alone, the degradation of hydrocarbons by microorganisms is much better, if the two materials are utilized conjointly, the total concentration of assimilable nitrogen being the same.

Thus, microemulsions according to the invention allow a degradation of more than 80% of crude petroleum distributed on seawater to be obtained, for example, in seven days, when the nutrient solution contains urea or amino-acids. But the same result is obtained in six days, if the urea and the amino-acids are present conjointly in the solution, the total nitrogen concentration thereof being the same as in the two preceding cases.

The invention is illustrated by the series of non-limitative examples which follow.

EXAMPLES 1 TO 11

For each of the tests, a certain volume of a 50% by weight aqueous urea solution was mixed with a volume of oleic acid in the presence of a certain quantity of surfactants constituted by a mixture of $C_{12}$ to $C_{18}$ fatty alcohol phosphoric esters marketed by Hoechst Company under the name "Hostaphat". In certain of the tests, the butyl ether of ethylene glycol was also added to lower the viscosity. The range of temperatures in which the microemulsion obtained was stable was determined.

Table 1 on the following page indicates the compositions of the microemulsions so prepared, the stability ranges of the latter and their viscosity. It can be seen that an excellent stability in the range from 0° C. to more than 40° C. can be obtained according to Examples 4, 5, 6, 8, 10 and 11. As regards viscosity, it was found that, without the addition of the butyl ether of ethylene glycol, it is very high (Examples 1 and 2). In contrast, this addition reduces it to very acceptable values (Examples 3 to 11).

TABLE 1

|  | 1 | 2 | 3 | 4 | 5 | 6 | 7 | 8 | 9 | 10 | 11 |
|---|---|---|---|---|---|---|---|---|---|---|---|
| Water | 11.1 | 11.7 | 13.8 | 14.4 | 18.3 | 20.1 | 20.9 | 21.9 | 19.2 | 20.2 | 19.2 |
| Urea | 11.1 | 11.7 | 13.8 | 14.4 | 18.3 | 20.1 | 20.9 | 17.2 | 15.8 | 16.6 | 15.7 |
| Oleic Acid | 44.4 | 46.7 | 36.8 | 38.4 | 36.6 | 32.1 | 27.9 | 27.9 | 28 | 29.4 | 28 |
| Butyl ether of ethylene glycol | 0 | 0 | 10.6 | 9.8 | 10.7 | 11.6 | 14.4 | 14.4 | 17.5 | 16.2 | 10.5 |
| Lauryl Phosphate (KL 340) | 33.3 | — | 25 | — | — | — | — | — | 19.5 | 8.8 | 19.5 |
| Oleyl Phosphate (KO 380) | — | 30 | — | 23 | — | — | — | — | — | — | — |
| Ethoxylated Phenol Alkyl Phosphate | — | — | — | — | 16.1 | 16.1 | 15.9 | 15.9 | — | 8.8 | — |
| Mono Ammonium Phosphate | — | — | — | — | — | — | — | 2 | — | — | — |
| % Nitrogen | 5.2 | 5.45 | 6.44 | 6.72 | — | — | — | — | 7.4 | — | — |
| Nitrogen/Oleic acid ratio | 0.117 | 0.117 | 0.175 | 0.175 | 0.23 | 0.29 | 0.35 | 0.31 | 0.26 | 0.26 | 0.26 |
| Phosphorus/Nitrogen ratio | 0.154 | 0.064 | 0.09 | 0.043 | 0.099 | 0.09 | 0.086 | 0.063 | 0.064 | — | — |
| Stability Range °C. | 10–44 | 10–46 | 1–44 | 0–44 | 0–40 | 0–47 | 12–57 | 0–40 | 0–36 | 0–42 | 0–45 |
| Viscosity in cps at 20° C. | 1200 | 2000 | 167 | 265 | 203 | 197 | 141 | 98 | 61 | — | — |

EXAMPLES 12 TO 16

Microemulsions were prepared with 33% lauryl phosphate. The lipomiscible liquid was oleic acid in a quantity equal to twice that of the aqueous solution of urea and phosphate. The percentage of urea in the aqueous phase was varied. The results below give the maximum temperature at which the microemulsion was still stable.

| % Urea in the aqueous phase | Upper limit of the temperature °C. |
|---|---|
| 22.2 | 36 |
| 25 | 32 |
| 33 | 38 |
| 50 | 35 |
| 56 | No microemulsion |

The results show that microemulsions viable in practice, stable up to about 36° C. can be obtained with concentrations of urea ranging up to 50%, but not above that.

EXAMPLES 17 TO 19

With a 50% aqueous solution of urea and the addition of oleyl phosphate containing 30% of the monoethyl-ether of ethylene glycol, three microemulsions were prepared containing varying proportions of oleic acid. The stability ranges of these products were as follows:

| Weight ratio of the urea oleic acid solutions | Surfactant (Oleyl phosphate) | Stability range °C. |
|---|---|---|
| 0.5 | 25.3 | 0–65 |
| 0.625 | 24.2 | 0–59 |
| 0.75 | 26.7 | 0(gel)–64 |

This shows that above an aqueous solution/oleic acid ratio of about 0.65 and for a fixed quantity of the monoethyl-ether of ethylene glycol of 30%, the microemulsion is difficult to utilize because it tends to gel. In contrast, below this ratio, excellent stability is confirmed.

DEGRADATION OF PETROLEUM HYDROCARBONS

EXAMPLE 20

30 l of seawater sterilized at 120° C. for 2 hours was introduced into a 50-liter fermenter. On the surface of the seawater, 30 ml of 34° API crude petroleum containing 75% saturated hydrocarbons and 25% aromatics was spread out. The petroleum layer had a thickness of 0.5 mm. On this layer, 6 ml of one of the microemulsions of the foregoing Examples was atomized. The medium was thus seeded with sources derived from the seawater. These sources were obtained by culturing for 24 hours on an aqueous solution of glucose. They contained Pseudomonas in a major part.

After this inoculation, the sources in the petroleum samples were assayed; $2.5 \times 10^3$ to $4 \times 10^4$ microbes per ml were thus formed.

Aerobic culture was then carried out by agitating the contents of the fermenter with an agitator rotating at 400 revs per min, while 120 liters of sterilized air per hour were blown in. This aeration corresponds substantially to that which takes place naturally at sea.

After 40 hours, a further assay was effected. The results are indicated below.

After seven days, the rate of degradation of the petroleum was determined by extraction of the residual hydrocarbons with $CCl_4$ and infrared measurement. The results obtained with the microemulsions of Examples 1, 2, 3, 10 and 11 are indicated below.

| Microemulsion of | Initial source | Source assay after 48 hours | Rate of degradation after 7 days |
|---|---|---|---|
| Ex. 1 | $2.5 \times 10^3$ | $2.5 \times 10^8$ | 83% |
| 2 | $2 \times 10^4$ | $9.5 \times 10^8$ | 90% |
| 3 | $1.5 \times 10^4$ | $2.5 \times 10^8$ | 90% |
| 10 | $4.5 \times 10^3$ | $2.5 \times 10^8$ | 86% |
| 11 | $1.5 \times 10^3$ | $7.5 \times 10^7$ | 92% |

EXAMPLE 21

A test was carried out according to the mode of operation described in Example 20, but non-sterilized seawater are introduced into the fermenter and the medium was not seeded with supplementary bacteria.

The results are:

| Microemulsion of | Initial source | Source assay after 40 hours | Rate of degradation after 7 days |
|---|---|---|---|
| No 11 | $2 \times 10^3$ | $5.5 \times 10^7$ | 82% |

EXAMPLE 22

A test was carried out according to the mode of operation of Example 20, but the seawater was replaced by natural water into which various mineral constituents of seawater had been added, namely 30 ppm of trace elements, particularly iron, magnesium and potassium. 6 ml of microemulsion No. 11 was atomized and the medium was seeded with a culture of bacteria.

After 7 days, the rate of degradation of the petroleum was determined by extraction of the residual hydrocarbons with $CCl_4$ and infrared measurement; the rate was 90%.

EXAMPLES 23 TO 24

Biodegradation tests on crude Arabian petroleum were effected at the edge of the sea in a vessel having a depth of 2 meters, divided into four compartments each 3 m×3 m in horizontal section. The compartments could be isolated or connected together and all were capable of receiving seawater.

A hydro-ejector pump system ensured light agitation of the water and renewal of the air in the vessel.

Into each compartment, 15.6 m³ of seawater and 4 liters of the petroleum indicated above were introduced, thus providing a layer 0.45 mm thick on the surface of the water.

One of the compartments served as a control; the water and the petroleum contained in it were agitated as in the other compartments, but received no additive. At the end of the test, the losses of petroleum due to natural causes were determined in order to take them into account in evaluation of the degradation caused by the additions according to the invention.

In each of the three other compartments, 0.4 l of a microemulsion of a nutrient solution was introduced, comprising in % by weight:

| | |
|---|---|
| urea | 17.0 |
| clear water | 20.8 |
| butyl glycol | 10.8 |
| lauryl phosphate | 21.1 |
| oleic acid | 30.3 |

At the start of the test, the microflora of the seawater in the tank comprised $10^2$ bacteria per ml. After 7 days the quantities of petroleum which had disappeared from the compartments were determined. The Table below indicates the amounts in % of the initial quantity at two different temperatures.

| | Control 12° C. | Example 23 12° C. | Control 18° C. | Example 24 18° C. |
|---|---|---|---|---|
| % of disappearance due to natural causes | 5 | 5 | 17.5 | 17.5 |
| % due to treatment according to the invention | 0 | 58 | 0 | 61.3 |
| % total disappearance | 5 | 63 | 17.5 | 78.8 |

As can be seen, even at the relatively low temperature of 12° C., the biodegradation obtained in seven days by the treatment of the invention is remarkable. In contrast to most of the known processes without the use of a culture of microorganisms, this was obtained with the sole use of those existing in the seawater.

EXAMPLE 25

30 ml of seawater were introduced into a 50-liter fermenter. On the surface of this water, there was spread 30 ml of crude 34° API petroleum, containing 75% of saturated hydrocarbons and 25% aromatics. On the petroleum layer thus formed, having a thickness of 0.5 mm, 6 ml of the microemulsion having the following weight composition was atomised:

| | |
|---|---|
| urea | 17.3% |
| water | 21.5 |
| butyl ether of ethylene glycol | 10.8 |
| lauryl phosphate | 23.7 |
| oleic acid | 26.7 |
| (8.07% of nitrogen) | 100.0 |

Assay of the bacteria in the petroleum indicated the presence of $10^2$ bacteria per ml.

Aerobic culture was then carried out by agitating the contents of the fermenter with an agitator rotating at 400 revs per min while 120 liters of sterilized air per hour were blown in. This aeration corresponded substantially to that which takes place naturally at sea.

After 48 hours, a new assay was effected. It showed the presence of $2.5 \times 10^8$ bacteria per ml.

After 7 days, the rate of degradation of the petroleum was determined by extraction of the residual hydrocarbons with $CCl_4$ and infrared measurement. This rate was 83%.

EXAMPLE 26

Identical operations to those of Example 25 were effected, but in the microemulsion a part of the urea was replaced by the amino-acid DL-valine. The weight composition of the microemulsion was:

| | |
|---|---|
| urea | 16.8% |
| DL-valine | 2.0 |
| water | 20.5 |
| butyl ether of ethyleneglycol | 10.8 |
| lauryl phosphate | 23.7 |
| oleic acid | 26.2 |
| | 100.0 |

(total nitrogen, of the urea and valine, 8.07%)

Bacterial assay gave the number as $10^2$ at the start and $10^9$ after 48 hours. The rate of degradation of the petroleum was 84% by the sixth day.

Comparison with Example 25 shows that addition of the amino-acid allowed $10^9$ bacteria to be obtained in place of $2.5 \times 10^8$ with urea alone after 38 hours. The degradation was of the same order (84% against 83%), but was obtained more rapidly, in six days, whilst it was necessary to provide 7 days in the case of urea alone.

EXAMPLE 27

According to the technique of Examples 25 and 26 a microemulsion was utilized in which a part of the urea was replaced by an aqueous extract of maize cobs containing a series of amino-acids, predominantly alanine, arginine, glutamic acid and leucine. Other amino-acids present in lesser proportions were proline, isoleucine, threonine, valine, phenyl-alanine, methionine and cystine. The total nitrogen content in this extract was 1%.

The microemulsion had the weight composition:

| | |
|---|---|
| urea | 12.4% |
| corn-cob extract | 18.7 |
| butyl ether of ethyleneglycol | 19.2 |
| lauryl phosphate | 29.1 |
| oleic acid | 20.6 |

The water of the aqueous phase was that of the aqueous extract. The total nitrogen content of the aqueous phase amounted to 6%.

Starting at $10^2$ bacteria, they numbered $4 \times 10^9$ after 48 hours and the rate of degradation of the petroleum had attained 88% after six days.

Comparison of these results with those of Example 25 shows the desirability of the addition of amino-acids to urea.

EXAMPLES 28 TO 37

In this series of tests analogous to Example 27, the lauryl phosphate was replaced by oleyl phosphate and oleic acid by various liquids indicated in the following table, which gives the rate of degradation of petroleum obtained after 6 days.

| Example No | Hydrophobic liquid utilized | Degradation % |
|---|---|---|
| 28 | Arachidic oil | 88 |
| 29 | Rape oil | 82 |
| 30 | Tall oil | 86 |
| 31 | Mixture of coconut fatty acids with 10% oil of vaseline | 85 |
| 32 | Lauric acid liquefied with 10% of crude petroleum | 84 |
| 33 | Butyl caproate | 85 |
| 34 | Ethyl laurate | 87 |
| 35 | Methyl oleate | 86 |
| 36 | Amyl stearate | 88 |
| 37 | Gas oil with 10% sesame oil | 83 |

Similar results are obtained with a mixture of $C_{12}$–$C_{14}$ alkyl mono-, di- and tri(alkyltetraglycolether)-o-phosphates, known commercially under the name "HOSTAPHAT KL 340 N", instead of oleyl phosphate.

We claim:

1. A nutrient liquid composition intended to be added to a hydrophobic medium for the culture of microorganisms therein comprising a microemulsion of an aqueous solution of nutrient material in a liquid immiscible with water, the aqueous solution being the internal phase of the microemulsion, said microemulsion comprising by weight 10-30% of water, 4-10% of microorganism assimilable nitrogen in the form of nitrogenous compounds, 5-35% of a 10-18 carbon atom alkyl or alkenyl phosphate or an epoxylated phenol alkyl phosphate, 0-20% of an alkyl ether of an alkylene glycol and 20-50% of a fatty acid ester, acid or alcohol or mixture thereof with a petroleum derivative hydrocarbon.

2. Composition according to claim 1, wherein the nitrogenous compound comprises urea.

3. Composition according to claim 2, wherein the urea is present in the aqueous solution at a concentration of 10-60% by weight.

4. Composition according to claim 3, wherein said urea solution contains an amino acid.

5. Composition according to claim 4, in which the urea nitrogen is 50-99% of the total nitrogen present.

6. Composition according to claim 5, in which the amino acid is at least one member of the group consisting of glycine, alamine, serine, cysteine, valine, glutamine, leucine, lysine, argynine, proline, tyrosine, aspartic acid and glutamic acid.

7. Composition according to claim 5, in which said microemulsion contains 20-50% of a mixture of a fatty ester, acid or alcohol with a petroleum derivative hydrocarbon in which the petroleum derivative hydrocarbon is 5-90% thereof.

8. Composition according to claim 1, wherein the nitrogenous compound is at least one member selected from the group consisting of ammonium sulphate, ammonium phosphate, lecithin and urea.

9. Composition according to claim 8, in which at least two nitrogenous compounds are present, one of which is urea.

10. Composition according to claim 1, in which said microemulsion contains 20-50% of a mixture of a fatty ester, acid or alcohol with a petroleum derivative hydrocarbon in which the petroleum derivative hydrocarbon is 5-90% thereof.

11. Composition according to claim 1, in which the external phase of the microemulsion is a lipomiscible organic liquid containing compounds of carbon assimilable by microorganisms.

12. Composition according to claim 1, in which the phosphorus to nitrogen weight ratio is from 0.02 to 0.2.

13. Composition according to claim 12, wherein said ratio is from 0.05 to 0.15.

14. Composition according to claim 13, wherein said ratio is about 0.05.

15. Composition according to claim 1 containing 5-8% of assimilable nitrogen.

16. Composition according to claim 1 in which the fatty acid ester, acid or alcohol comprises oleic acid.

17. Composition according to claim 1 in which said microemulsion comprises water, urea, oleic acid and oleyl phosphate.

18. Composition according to claim 1, wherein said microemulsion comprises water, urea, oleic acid, butyl ether of ethylene glycol and lauryl phosphate.

19. Composition according to claim 1, wherein said microemulsion comprises 13.8-19.2% water, 13.8-15.7% urea, 28-36.8% oleic acid, 10.5-10.6% butyl ether of ethylene glycol and 19.5-25% of lauryl phosphate.

20. Composition according to claim 1 in which the internal phase is droplets of 80-600 Angstroms in diameter.

* * * * *